United States Patent [19]

Scharton et al.

[11] Patent Number: 4,700,134

[45] Date of Patent: Oct. 13, 1987

[54] METHOD AND APPARATUS FOR DETERMINING THE AMOUNT OF MAGNETIC DEBRIS ADHERING TO THE EXTERIOR OF A TUBE

[75] Inventors: Terry D. Scharton, Santa Monica; George B. Taylor, Culver City; Charles Kidd, Mission Hills, all of Calif.

[73] Assignee: Anco Engineers, Inc., Culver City, Calif.

[21] Appl. No.: 690,459

[22] Filed: Jan. 10, 1985

[51] Int. Cl.$^4$ .................... G01N 27/72; G01N 27/82; G01R 33/12; G01R 35/00

[52] U.S. Cl. ................................. 324/220; 324/202; 324/232

[58] Field of Search ................ 324/219–221, 324/229–231, 239–243, 232, 227, 202

[56] References Cited

U.S. PATENT DOCUMENTS 2,677,802  5/1954  Irwin .................................. 324/232
3,532,969 10/1970  McCullough et al. ............. 324/229
4,088,946  5/1978  Charles et al. ..................... 324/220

FOREIGN PATENT DOCUMENTS 1591443  6/1981  United Kingdom ................ 324/220

OTHER PUBLICATIONS

Lord et al., "Magnetic Probe Inspection of Steam Generator Tubing", Materials Evaluation, May 1980, pp. 838–840.

Primary Examiner—Reinhard J. Eisenzopf
Assistant Examiner—Walter E. Snow
Attorney, Agent, or Firm—Thomas I. Rozsa

[57] ABSTRACT

A method and apparatus for magnetically measuring the amount and location of magnetite ($Fe_3O_4$) debris adhering to the exterior of heat exchanger tubes which can be made of Inconel. A probe containing one or more coils of electrical wire is used to traverse the interior of the subject tube. One of the probe coils is energized with direct electric current to magnetize the magnetite coating on the tube exterior as the probe traverses the tube. The thickness of the magnetized coating is deduced from measurement of the voltage generated across a second coil of wire on a probe which traverses the tube at constant velocity.

8 Claims, 6 Drawing Figures (Demagnetized)

(Magnetized)

(Measured)

(Demagnetized)

METHOD AND APPARATUS FOR DETERMINING THE AMOUNT OF MAGNETIC DEBRIS ADHERING TO THE EXTERIOR OF A TUBE

BACKGROUND OF THE INVENTION

1. Field of the Invention

The present invention relates to a novel apparatus which is used to measure the quantity of magnetite which has adhered to the walls of heat exchanger tubes which are commonly found in the heat exchanger vessels of nuclear steam generators and are also found in other heat exchangers, boilers, condensers or the like. A description of the internal mechanism of a heat exchanger vessel in a nuclear steam generator can be found in U.S. Pat. No. 4,320,528 issued on Mar. 16, 1982 to inventors Terry D. Scharton and G. Bruce Taylor. As discussed in that patent, during the heat exchange process, the high temperatures combined with the liquid environment caused the steel support plates which supported the heat exchanger tubes to oxidize to magnetite. Magnetite, whose chemical formula is $Fe_3O_4$, was found at the juncture of the tube support plates and the heat exchanger tubes. The radioactive heat exchange process has also caused magnetite to form at other locations along the heat exchanger tubes. At the juncture of the heat exchanger tubes and support plates, the formation of magnetite caused denting and pinching of the tubes and eventually destroyed the usefulness of the tube which was dented or pinched. When magnetite forms at other locations along the heat exchanger tubes, the heat exchange process is impaired. It is therefore desirable to know how much magnetite has adhered to the heat exchanger tubes and the locations at which the magnetite has adhered.

In the example of nuclear steam generators, the heat exchanger vessel may contain as many as sixteen thousand thin walled, small bore tubes. By way of example, such tubes may have an outer diameter of approximately ⅜th of an inch and be sixty (60) feet long. They are also very tightly packed together inside the heat exchanger vessel. The only practical way to measure anything relating to these tubes is to place a very thin probe up one or more of the tubes and perform electronic measurements to determine the information that is desired. The present invention relates to the use of a novel type of probe to determine the locations along the length of one or more heat exchanger tubes where magnetite has adhered and to further determine the quantity of magnetite which has adhered at each of these locations.

2. Description of the Prior Art

Several different types of apparatus are known in the prior art for determining various parameters and other information about heat exchanger tubes, pipelines, oil well shaft, etc. by placing a probe into the physical structure and performing certain operations to determine the desired information.

There are several different prior art apparatus which are known for determining the physical dimensions of heat exchanger tubes and which are also used to determine abnormalities such as dents, out-of-roundness, holes, tears, and other problems with the tubes. These prior art apparatus use a probe which measures variations in eddy currents to determine the location and size of such abnormalities. An eddy current is an electric current induced by an alternating magnetic field. An eddy current is generated by a probe placed into and moved within the heat exchanger tubes, and the variation in the eddy current is combined with other data to determine the location and size of the abnormality. For example, the coil through which a sinusoidal current passes produces an electromagnetic field which induces eddy currents within the heat exchanger tube. These currents produce on return an alternating field which is set up in opposition to the initial field and then modifies the impedance of the coil. Any discontinuity which is present within the tube at the level of the probe modifies the path or intensity of the eddy currents. The defect is measured by various well known methods. Several prior art patents which address this type of art are:

1. U.S. Pat. No. 4,153,875 issued on May 8, 1979 to Pigeon et al. for "Eddy-current Testing Device for Metal Tubes Which Are Bent at Least Locally".

2. U.S. Pat. No. 4,325,026 issued on Apr. 13, 1982 to Cooper, Jr. et al. for "Plural Coil Eddy Current Mapping Probe".

3. U.S. Pat. No. 4,341,113 issued on July 27, 1982 to Gutzwiller, Jr. for "Inspection System for Heat Exchanger Tubes".

This method and apparatus is also discussed in informational literature prepared by Zectec, Inc., locted at 1320 N. W. Mall, Issaquah, Wash. 98027.

Other apparatus known in the prior art are used to test for magnetic material within long shaft like structures. U.S. Pat. No. 4,330,748 issued to Holden on May 18, 1982 for "Frequency Correction Circuitry for Pipeline Sensor Apparatus" discloses an apparatus used for the non-destructive testing of ferromagnetic materials in pipelines which are buried below the ground or submerged in water. An inspection vehicle is run along the outside of the pipeline which contains a probe containing an electromagnetic sensor to produce an electrical signal in response to variations in the magnetic field in the vicinity of the sensor and various electronic components to measure the magnetic signal read by the probe. U.S. Pat. No. 4,023,092 issued to Rogers on May 10, 1977 for "Apparatus for Sensing Metals in Wells" discloses an apparatus which located ferrous objects in well bores such as casings, collars and the like. U.S. Pat. No. 2,677,802 issued to Irwin on May 4, 1954 for "Method and Apparatus for Demagnetizing Material" relates to a method and apparatus for electrically testing the properties of materials which includes demagnetizing the material.

The apparatus in the prior art which comes closest to the present invention is disclosed in U.S. Pat. No. 4,088,946 issued to Charles et al. on May 9, 1978 for "Magnetic Bridge Transducer Formed with Permanent Magnets and a Hall Effect Sensor for Identifying the Presence and Location of Ferromagnetic Discontinuities Within or on a Tubular Specimen". The apparatus includes a probe which is placed inside heat exchanger tubes to measure magnetite. Although the object of this prior art apparatus is the same as the present invention, the specific technology employed is different. A key element of this prior art apparatus is a transducer which generates a magnetic field which can be placed in magnetic communication with and is movable over a portion of the surface area of the heat exchanger tube. A Hall element within the transducer is fixedly positioned with respect to the source of the magnetic field and arranged to be placed in magnetic communication with the specimen. The output of the Hall element which provides the transducer response is representative of the strength of the magnetic field having a component contribution from lines of force proximate and perpendicular to a given plane of the Hall element. Basically, in this prior art apparatus, the apparatus balances magnetic fields, within the probe itself, in such a way that a zero magnetic field is sensed at the Hall element when the probe is remote from external ferromagnetic materials. When a probe, initially balanced in this manner, is brought near a ferromagnetic material, the resulting electrical signal is a direct measure of the perturbation produced in the magnetic field and hence is also a measure of a quantity of ferromagnetic material present.

None of the apparatus disclosed in the prior art provides an effective and efficient means for measuring the quantity of magnetite which has adhered to heat exchanger walls. The apparatus in the Charles patent which employs a Hall element is subject to several inaccuracies. The major problem with the Hall element is that it measures an absolute magnetic field and does not allow for adjustments to particular environments such as different heat exchanger tubes which have different diameters, wall thicknesses and are made of different materials. In addition, the Hall element is subject to inaccuracies which result from variations of temperature and other properties in the environment.

In view of the difficult operating conditions under which workers must perform their tasks relating to measuring magnetite in the heat exchanger of the nuclear steam generator, it is necessary to provide an apparatus which is both simple and accurate and which permits measurements to be made at a location remote from the heat exchanger vessel. The embodiments in the prior art do not teach or make obvious such a device.

SUMMARY OF THE PRESENT INVENTION

The present invention relates to a novel method and apparatus for measuring the quantity of magnetite which has adhered to the heat exchanger tubes in vessels such as the heat exchanger of a nuclear steam generator or a boiler, condenser or the like. The present invention utilizes the fact that magnetite has magnetic properties since its chemical composition if $Fe_3O_4$ and is capable of being magnetized. The present invention also utilizes the fact that the amount of magnetic flux associated with a given quantity of magnetite is proportional to the amount of magnetic flux associated with the substance. As a result, if voltage can be determined by moving a coil through a quantity of magnetite, then the amount of magnetite through which the coil has been moved can be determined. The present invention also utilizes the fact that the amount of magnetism which can be induced into a given quantity of magnetite is affected by the diameter of the tube, the thickness of the tube, and the substance out of which the tube is made when the magnetite has adhered to the outer surface of the tube.

The concept of the present invention is to provide a method for charting the amount of magnetite which has adhered to the outer surface of a tube whose diameter, wall thickness and material are known. Sample tubing comparable to that found in the heat exchanger to be tested is provided with different thicknesses of magnetite along its length. The sample tubing and adhered magnetite is then magnetized by a known amount of magnetic flux. A coil is then moved through the tube and the voltage at different thicknesses of magnetite is recorded. Since the voltage is proportional to the amount of magnetic flux contained in the magnetite and the amount of magnetic flux is proportional to the thickness of the adhered magnetite at a given location, a chart can be calculated which shows the given voltage generated in a coil by the magnetic flux associated with a given thickness of magnetite in the particular type of tubing from which the sample is made. As a result, a table of calibration constants can be established for a given tubing of a given diameter, wall thickness and material. Once the table has been established, the present invention utilizes a novel probe to calculate the quantity of magnetite which has adhered along the length of heat exchanger tubes of the same diameter, wall thickness and material as the sample tubing on which given calibration constants have been tabulated. The probe of the present invention consists of three separate sections. The first section contains means to demagnetize the magnetite which has adhered to heat exchanger tubes. The purpose of demagnetizing the magnetite is to start at a known zero level. The second section contains means to magnetize the magnetite so that the adhered magnetite will now contain a quantity of magnetic flux. The third section contains voltage generating means such that a quantity of voltage is generated within the third section and is measured by measuring means connected to the third section. Based on the calibration table, once the quantity of induced voltage is known, the amount can be correlated to the thickness of magnetite required to induce such a voltage.

It has been discovered, according to the present invention, that if a calibration table is computed which indicates the amount of magnetite needed to induce a given voltage within a coil when the magnetite has adhered to tubing of known diameter, wall thickness and material, then a novel probe containing means to demagnetize the magnetite, remagnetize the magnetite, and measure the voltage induced by the magnetized magnetite when the coil is moved through the heat exchanger tube to which the magnetite has adhered can be used to accurately measure the quantity and thickness of the magnetite along the length of the tubing.

It has also been discovered, according to the present invention, that the above described method and apparatus provide a very sensitive and accurate apparatus for measuring the quantity and thickness of magnetite which has adhered at varying positions along the length of the heat exchanger tube. This provides a substantial advantage over prior art devices which incorporate a Hall element that can vary with temperature and pressure.

It has further been discovered, according to the present invention, that if a calibration table for a given environment is produced and a probe as previously described is used to measure induced voltage and then magnetite thickness, the method and apparatus are accurate regardless of varying temperatures, moisture and other unfavorable elements in the environment being measured. This is a substantial improvement over Hall effect devices which measure only absolute magnetic fields and are subject to inaccuracies caused by temperature fluctuations and drift.

It is therefore an object of the present invention to provide a method of accurately calibrating the quantity of voltage induced in a coil which is moved through a heat exchanger tube to which magnetite has adhered and has been magnetized, to thereby accurately determine the quantity and thickness of magnetite at varying locations along the length of the tube.

It is another object of the present invention to provide a means for calibrating voltage induced by magnetized magnetite for specific types of heat exchanger tubing, taking into consideration various parameters of the tubing such as diameter, wall thickness and material out of which the tubing is made.

It is a further object of the present invention to provide an accurate means for measuring the quantity and thickness of magnetite which has adhered to heat exchanger tubes such that the measuring instrument is not affected by environmental factors such as temperature.

Further novel features and other objects of the present invention will become apparent from the following detailed description, discussion and the appended claims, taken in conjunction with the drawings.

DRAWING SUMMARY

Referring particularly to the drawings for the purpose of illustration only and not limitation, there is illustrated:

DETAILED DESCRIPTION OF THE PREFERRED EMBODIMENT

Figure 1:
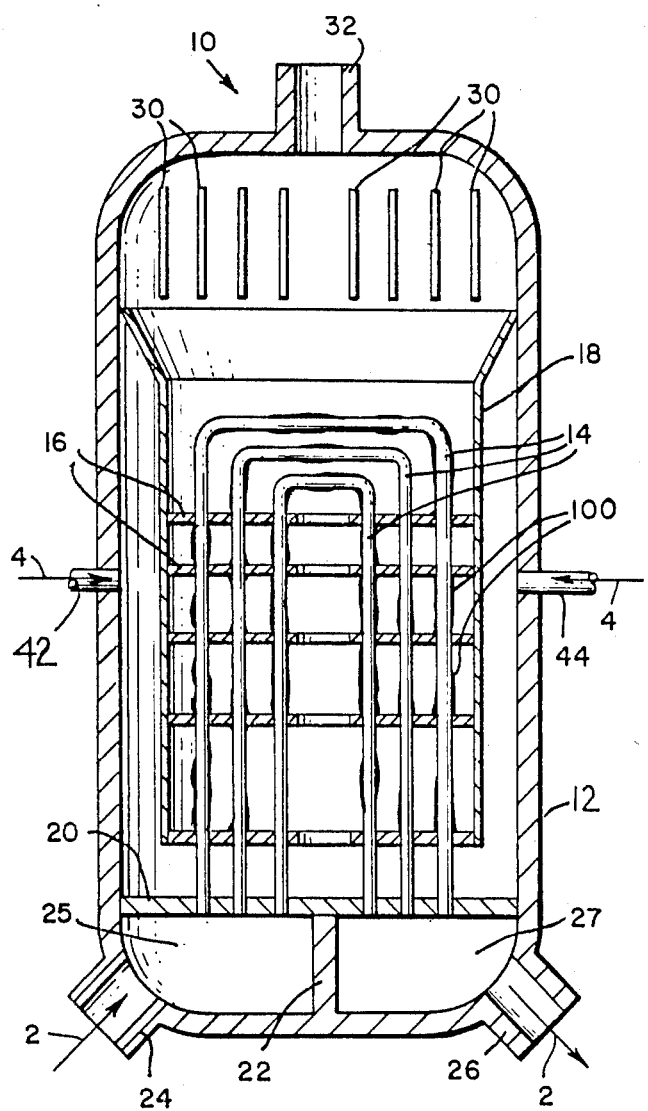
FIG. 1 is a side sectional view of a typical heat exchanger.

Although the apparatus and method of the present invention will now be described with the reference to specific embodiments in the drawings, it should be understood that such embodiments are by way of example and merely illustrative of but a small number of the many possible specific embodiments which can represent applications of the principals of the invention. Various changes and modifications obvious to one skilled in the art to which the invention pertains are deemed to be within the spirit, scope, and contemplation of the invention as further defined in the appended claims.

FIG. 1 discloses a heat exchanger vessel commonly found in a nuclear steam generator. The steam generator or heat exchanger is designated as 10. The external shell or envelope 12 of said heat exchanger is a pressure vessel. Inside this external shell 12 are a large number of heat exchanger tubes 14 which are the tubes that carry the primary fluid within the primary system of said heat exchanger. The heat exchanger tubes 14 pass through a multiplicity of support plates 16 which are located along the length of the heat exchanger tubes 14 and which encircle each heat exchanger tube 14 so as to form a means for separating one tube from the next and allowing each tube to remain in a fixed position within the tube bundle. The support plates 16 are in turn contained within a cylindrical iron wrapper 18. The heat exchanger tubes 14 are typically made of a nickel alloy such as inconel, and number from 10,000 to 16,000. Each heat exchanger tube 14 ranges from ½ inch to ⅞ inch outer diameter and are approximately 50 mils in thickness. The heat exchanger tubes 14 are connected at their bottom end to an apertured plate or tube sheet 20.

In normal operation, the primary fluid 2 comes from a heat source such as a nuclear reactor and enters the heat exchanger 10 through a primary entrance nozzle 24. The fluid enters into the area between the bottom of the pressure vessel external shell 12 and the tube sheet 20. A separating wall 22 separates the inlet side 25 of the heat exchanger 10 from the outlet side 27. The primary fluid 2 which comes from a heat source such as a nuclear reactor carries heat with it as it is forced through the various tubes 14 and up through the heat exchanger 10. The heat exchanger 10 illustrated in FIG. 1 is of the U-bend type, where the tubes 14 run most of the length of the heat exchanger 10 and are bent at the top to form a U-shaped configuration. The U-shaped tubes 14 are attached at their bottom to the tube sheet 20 which is mounted to the back of the external shell 12 of the heat exchanger 10, and thereby define the primary system of the heat exchanger 10. Upon reaching the uppermost portion of the tubes 14, the primary fluid 2 starts back down the opposite side of the tubes 14 and exits the heat exchanger 10 through the primary outlet nozzle 26 on the outlet side 27 of the heat exchanger 10.

Heat which is carried by the primary fluid 2 is transferred to the secondary fluid 4 while the primary fluid 2 is circulating through the tubes 14. The secondary fluid 4 enters the heat exchanger 10 through secondary inlets 42 and 44 located in the external shell 12 and is located in the area surrounding the tubes 14 and within the external shell 12. Sufficient heat is transferred to the secondary fluid 4 so that the primary fluid 2 exiting the primary outlet nozzle 26 is at a substantially lower temperature than it was when it entered the heat exchanger through primary inlet nozzle 24. The secondary fluid 4 absorbs heat carried by the primary fluid 2 and the secondary fluid 4 becomes steam during the heat absorbtion process. The steam passes through separators 30 which remove excess moisture from the steam, and then exits through the steam outlet 32 at the top of the heat exchanger 10. The high pressure steam can then be used to drive a turbine.

The secondary fluid 4, secondary inlets 42 and 44, separators 30, and steam outlet 32 define the secondary system of the heat exchanger 10.

The elevated temperatures and liquid environment in which all of the above occurs fosters oxidation of the various metal components of the steam generator. As a result, a spongy substance known as magnetite is created from the oxidation process. The chemical formula of Magnetite is $Fe_3O_4$. It contains iron and has magnetic properties. The magnetite 100 adheres to numerous locations on steam generator components. The areas of adherence with which the present invention is concerned are along various sections of the heat exchanger tubes 14, as shown in FIG. 1. The magnetite 100 adheres along the length of the heat exchanger tubes 14 as well as at the junction of the heat exchanger tubes 14 and support plates 16. At the location of the junction of heat exchanger tubes 14 and tube support plates 16, the magnetite 100 causes denting and pinching of the tubes 14. At other locations along the length of the heat exchanger tubes 14 the formation of the magnetite 100 impairs the heat transfer process previously described. It is therefore important to remove this magnetite 100. However, before all of the magnetite 100 can be effectively removed, it is necessary to know where the magnetite 100 is located. Since the tubes 14 number between 10,000 and 16,000 and are each 60 feet long, a visual inspection is not practical. In addition, the entire apparatus is radioactive and therefore a visual inspection would be dangerous as well as impractical. It is therefore necessary to have a method and apparatus which can accurately calculate the quantity of adhered magnetite in very adverse conditions and which permits such analysis to be made while the workers are at a location remote from the heat exchanger vessel.

Each heat exchanger will have a type of tube which is slightly different from other heat exchangers. In some heat exchangers, the tubes are of a certain diameter, wall thickness and material while other heat exchangers have tubes of differing diameter, wall thickness and material. It is therefore necessary to properly calibrate the specific tube for the particular heat exchanger which will be the subject of the measurement. Therefore, the first step in the method of the present invention is to obtain sample tubing of the same diameter, wall thickness and material as the tubing found in the heat exchanger on which measurements will be made. The sample tubing, which by way of example can be approximately one foot long, is then coated with varying thicknesses of magnetite at different areas along its length. Since the chemical formula of magnetite is $Fe_3O_4$, it is capable of being magnetized. It is known that the quantity of magnetic flux contained within the magnetite is proportional to the quantity and thickness of magnetite present. It is also known that if a coil is moved through a magnetic field, a voltage is induced in the coil. The voltage induced in a coil is proportional to the velocity with which the coil is moved through the magnetic field and is also proportional to the quantity of magnetic flux contained in the object through which the coil is moved. Therefore, in the form of equations:

$MF = k_1 MG$ $V = k_2 vMF$

Where:
MF = the magnetic flux;
MG is the thickness of magnetite;
V = Voltage induced in a coil moving through the magnetic field;
v = the velocity with which the coil is moved through the magnetic field;
$K_1$ and $K_2$ are calibration constants.
Therefore, $V = k_1 k_2 vMG$ If the thickness of magnetite (MG) is known and the velocity with which the coil is moved through the magnetic field is known, and the Voltage at the specific location is known, then the combined calibration constants $K_1 k_2$ for a specific tubing can be calculated. Therefore, a coil attached to a voltmeter is run through the sample tubing at a known velocity and readings of voltage at specific locations where a known thickness of magnetite which has been magnetized is read. From this information, the calibration constants $k_1 k_2$ can be calculated.

The inventors have performed experiments to prove that magnetite thickness affects the voltage induced in a coil run through a tube to which magnetite has adhered. Using a stainless steel tube approximately $\frac{5}{8}$ inches in inner diameter and $\frac{1}{8}$ inch in internal wall thickness, the following table shows voltage induced in the coil moved through the tube at various magnetite thickness locations on the tube:

| Magnetite Thickness (inches) | Voltage Induced (volts) |
| --- | --- |
| 0.02 | 0.04 to 0.07 |
| 0.01 | 0.02 to 0.04 |
| 0.015 | 0.04 to 0.07 |
| 0.040 | 0.18 to 0.25 |
| 0.077 | 0.40 to 0.61 |

Therefore, for a given type of heat exchanger tube of known diameter, wall thickness and made of a known type of material, if a coil is run through a magnetic field at a known velocity and a voltage is read at a specific location, the thickness of magnetite can be determined by the following formula:

$$MG = \frac{V}{k_1 k_2 v}$$

Figure 2:
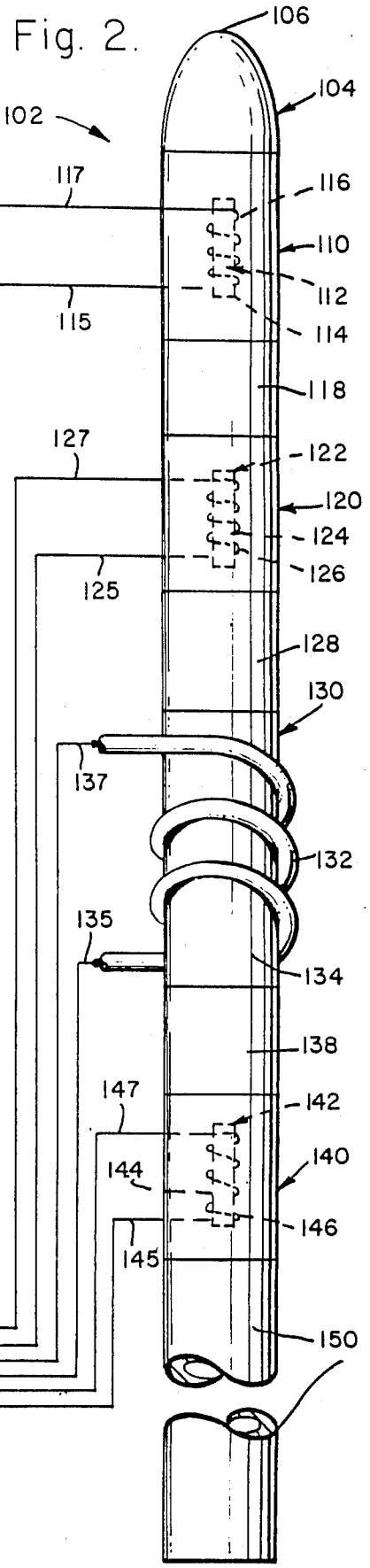
FIG. 2 is a side elevational view of the probe of the present invention.

The present invention incorporates this formula into use with a novel magnetic probe design. FIG. 2 shows a side elevational view of the probe 102. The probe includes three necessary sections and a fourth optional section in addition to a tip and a base. The top of the probe 102 contains a tip section 104 which is generally rounded at its nose 106. The tip section 104 is optional and is used to facilitate ease of insertion of the probe 102 into the heat exchanger tube 14. Located adjacent the tip 104 (or at the front end if there is no tip) is the first section 110. The first section 110 includes means 112 for demagnetizing the magnetite 100 which has adhered to the heat exchanger tube 14. The purpose of demagnetizing this magnetite is to start at a zero level and to eliminate random magnetic flux fields. By way of example, the demagnetizing means 112 can comprise a core member 114 surrounded by a coil of wire 116. By way of example, the core member 114 can be a ferrite core or an air core. By way of example, the coil of wire 116 can be varnished copper wire comparable to that used for transformers and can be 16 or 18 gauge. The wire 116 should be capable of handling current in the range of between approximately 2 amps and approximately 200 amps. Wires 117 and 115 connect the coil 116 to a source of alternating current 200 capable of generating current in the range of between approximately 2 amps and 200 amps. High amperage alternating current between approximately 2 amps and approximately 200 amps which can induce voltage such as up to 120 volts of alternating current is run through the coil of wire 116. By running this level of alternating current through the wire, as first section 110 is moved through the heat exchanger tube 14, the magnetic field in the magnetite 100 is neutralized. It is necessary to have alternating current in order to neutralize both north and south poles of magnetism.

After first section 110 is a spacer section 118. This spacer section is mandatory in some applications and optional in other applications, as will be explained hereinbelow. Beyond first spacer section 118 is second section 120. Second section 120 includes means 122 for magnetizing the magnetite by a known quantity of magnetic flux. In order to induce magnetism, the magnetizing means 122 must be a low voltage source of direct current or pulsed direct current. This induces a square wave type signal. By way of example, the magnetizing means can comprise a core member 124 surrounded by a coil of wire 126. By way of example, the core member can be a ferrite core or an air core. Wires 127 and 125 connect coil 126 to a source of direct current 200. By way of example, the coil of wire 126 can be 12 gauge wire. The source of direct current to which the coil of wire 126 is attached can be a direct current battery such as a 12 volt battery or a 12 volt capacitor bank. Alternatively, the source can be a source of 14 volt direct current or pulsed direct current. The purpose of the second section 120 is to provide the magnetizing means in order to supply a known quantity of magnetic flux into the magnetite 100.

After second section 120 is a second spacer section 128. As will be described hereinbelow, the second spacer section 128 is also mandatory in some applications and optional in other applications. Beyond second spacer section 128 is third section 130. Third section 130 includes a coil of very finely wound wire 132. The wire 132 is also wrapped around a core 134 which can be a ferrite core or an air core. It is necessary that the coil of wire 132 by very finely wound wire which by way of example can be in the range of between approximately 20 gauge to 80 gauge. The wire 132 is connected to a voltmeter 220 by wires 137 and 135. As an additional option, an amplifier can be connected between the wire 132 and the voltmeter. The purpose of the amplifier (not shown) is to take a small signal and boost it above the noise level of the environment. As the third section 130 is moved through the now magnetized magnetite 100 by being moved through the heat exchanger tube 14, the magnetic field of the magnetite 100 induces a voltage in the wire 132 which is read by the voltmeter. The calibration constants $k_1 k_2$ were calculated at a certain speed, such as 1 foot per second, and therefore the probe 102 is moved through the heat exchanger tube 14 at the same speed in order to maintain the accuracy of the calibration constants.

The above sections are the necessary sections of the probe 102. Beyond the third section 130 is an optional third spacer section 138. Beyond the third spacer section is an optional fourth section 140. Fourth section 140 includes second demagnetizing means 142. By way of example, second demagnetizing means 142 can include a core 144 and a coil of wire 146 through which alternating current is run. Wires 147 and 145 connect coil 146 to a source of alternating current 230 capable of generating current in the range of between approximately 2 amps and approximately 200 amps. The wire 146 can be 16 or 18 gauge wire and voltage up to 120 voltage and having high amperage such as between approximately 2 amps and 200 amps is run through the wire 146. The purpose of the optional fourth section 140 is to once again demagnetize the magnetite 100 in case future tests are to be run.

Finally, the last section (also optional) is the base member 150. Also depicted in FIG. 2 are wires running from the various sections. Wires 115 and 117 run from the coil 116 to a source of alternating current 200 (as previously described). Wires 125 and 127 run from the coil 126 to a source of direct current or pulsed direct current 210 (previously described). Wires 135 and 137 run from wire coil 132 to a voltmeter 220 (or to an amplifier and then to a voltmeter). If used, wires 145 and 147 run from coil 146 to a source of alternating current 230 (as previously described).

Figure 3:
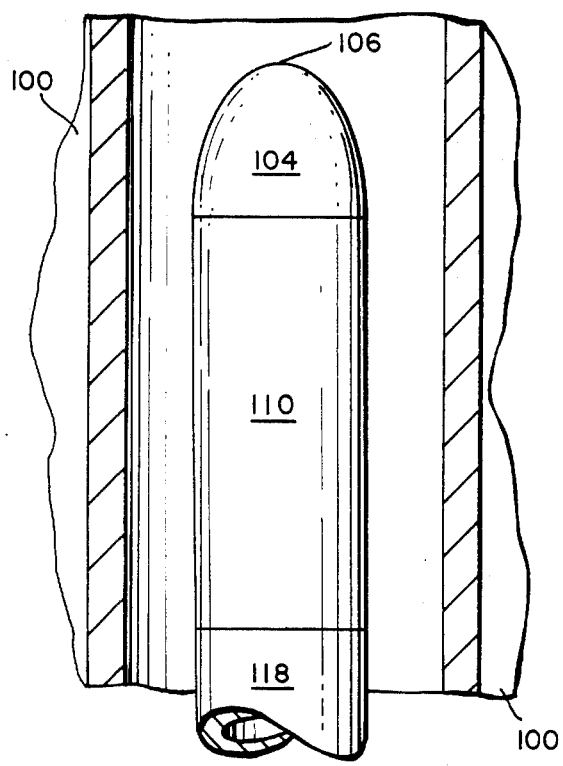
FIG. 3 is a fragmentary side elevational view of the first section of the present invention probe, inserted into a portion of a heat exchanger tube shown in partial cross-section.
Figure 4:
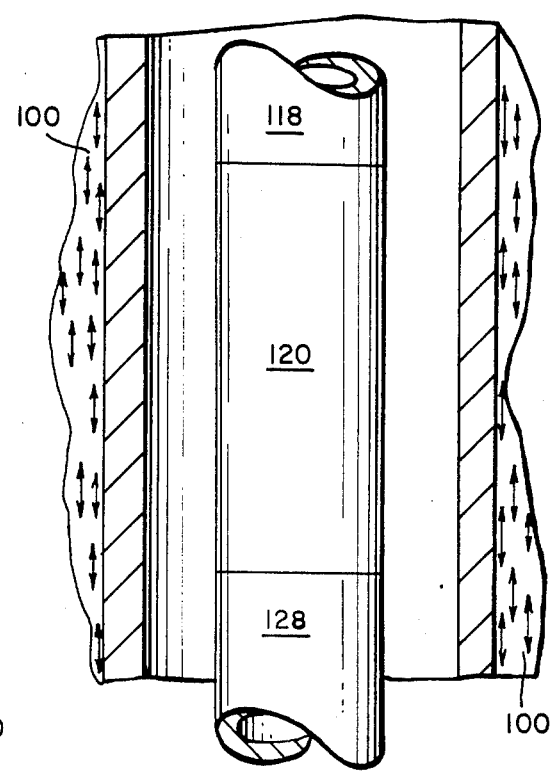
FIG. 4 is a fragmentary side elevational view of the second section of the present invention probe, inserted into a portion of a heat exchanger tube shown in partial cross-section.
Figure 5:
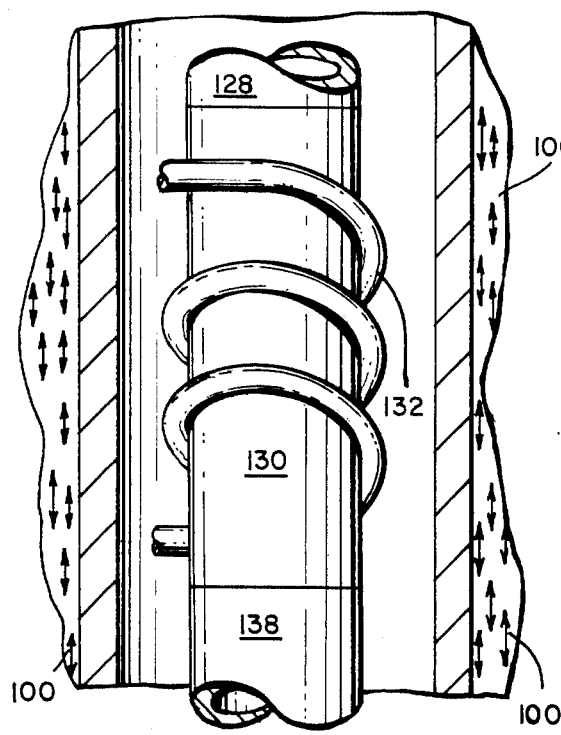
FIG. 5 is a fragmentary side elevational view of the third section of the present invention probe, inserted into a portion of a heat exchanger tube shown in partial cross-section.
Figure 6:
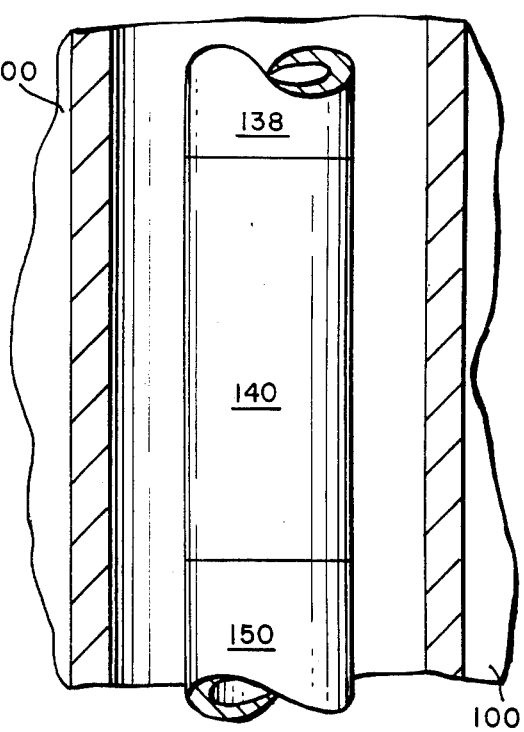
FIG. 6 is a fragmentary side elevational view of the optional fourth section of the present invention probe, inserted into a portion of a heat exchanger tube shown in partial cross-section.

There are several different types of methods by which the present invention can be used. For example, the probe is initially placed in a heat exchanger tube 14 through its tip section 104. This is shown in FIG. 3 which illustrates a fragmentary side elevational view of the tip section 104 and the first section 110 inserted into heat exchanger tube 14 which is shown in partial cross-section. The source of alternating current is turned on and the probe 102 is run up and down the tube 14 in order to demagnetize the magnetite 100 as previously described. After this operation, the source of alternating current is turned off. In the next phase, the source of direct current is turned on to energize magnetizing means 122 located in second section 120. This is shown in FIG. 4. The probe 102 is then run up and down the heat exchanger tube 14 in order to magnetize the magnetite 100 as previously described. After this operation, the source of direct current is turned off. The next operation involves running the probe 102 up through the heat exchanger tube 102 so that the magnetic field of the now magnetized magnetite 100 induces a voltage in fine coil 132. This is shown in FIG. 5. The probe 102 is moved through the tube 14 at a known velocity (preferably the same as that used to calibrate with as previously described) and at various sections the voltage is read by the voltmeter. By knowing the voltage, the velocity, and the calibration constants, the thickness of magnetite 100 at that location is determined by the equation previously set forth. This reading is continuously taken all the way along the length of the tube 14 in order to determine the magnetite thickness at various locations along the length of the tube 14. After the readings are completed, the fourth optional section 140 may be energized by running alternating current through coil 146 in order to once again demagnetize the magnetite 100. This is shown in FIG. 6. This operation is then repeated for each successive heat exchanger tube. In the type of heat exchanger depicted in FIG. 1, the probe 102 would be inserted from the open end of the tubes 14 which open into either chamber 25 or chamber 27. With the individualized method of using each section separately, as just described, the spacer members are not necessary.

An alternative more efficient method is to run two sections simultaneously. In this case, spacer members between sections are required in order for the operation of one section not to interfere with another section. It is therefore desirable for each spacer section to be at least six (6) inches long in order to properly separate one operating section from another. In this more efficient method, the alternating current source for coil 116 and the direct current source for coil 126 are activated simultaneously after the probe 102 is inserted into a heat exchanger tube 14. As the probe 102 is moved through the tube 14, the demagnetizing means 112 demagnetizes the magnetite 100 and the magnetizing means 122 thereafter magnetizes the magnetite 100 by the known quantity, as previously discussed. In this operation, it is necessary to have a first spacer section 118 between first section 110 and second section 120 so that the effectiveness of coils 116 and 126 do not interfere with each other. If by way of example first section 110 is approximately one (1) inch long and second section 120 is also approximately one (1) inch long, it would be desirable for first spacer section 118 to be approximately at least one (1) inch long. After the probe 102 has reached the top of the heat exchanger tube 14, both magnetizing means 112 and demagnetizing means 122 are turned off.

The voltmeter is then turned on and as the probe 102 is brought down the tube at a known velocity, the voltage induced in coil 132 is measured. As before, by knowing the voltage and velocity as well as the calibration constants, the thickness and quantity of magnetite 100 can be measured at each location along the length of tube 14.

Through use of the present invention, the quantity of magnetite 100 can be accurately measured without concern over varying temperatures and moisture as well as other problems with the environment in which the heat exchanger tubes are located. While the present invention has been described for use with heat exchangers in the steam generator of a nuclear reactor, the same principles can be utilized for boilers, condensers, and numerous other types of tube bundle heat exchangers.

The diameter of the heat exchanger tube should be larger than the diameter of the probe 102 in order to assure that the probe 102 can move smoothly within the tube 14. By way of example, the diameter of the probe 102 can be approximately one half ($\frac{1}{2}$) inch if the diameter of the heat exchange tube is approximately five eights ($\frac{5}{8}$) of an inch.

In the second embodiment of operation, where the magnetizing and demagnetizing means are activated while the probe 102 is moving in one direction and the voltmeter 26 read to determine induced voltage while the probe 102 is moving in the opposite direction, second spacer member 128 is also desirable. If the third section 130 is also approximately one (1) inch long, then second spacer section 128 can be at least approximately one (1) inch long.

Through use of the present invention, the coil 132 produces a voltge signal proportional to the rate of change of magnetic flux to thereby provide a very accurate and consistent reading. Once the thickness of magnetite is determined at various locations, means for removing the magnetite can be implemented, depending on the thickness and the location. Magnetite 100 encrusted at a junction of a heat exchanger tube 14 and tube support sheet 16 involves a more difficult removal process than magnetite 100 which has adhered to a section of tube 14 between support plates 16.

The present invention has been described with a probe containing all of the elements set forth above. It is also within the spirit and scope of the present invention to utilize three separate probe members. The first probe member would contain means for demagnetizing the magnetite and would be comparable to the first section 110 of probe 102. The first separate probe would contain demagnetizing means such as a core member surrounded by a coil of wire and connected to a source of alternating current as previously described. The second individual probe would contain elements comparable to the second section 120 of probe 102 for magnetizing the magnetite. By way of example, the second individual probe element could contain a core and a coil and be connected to a source of direct current, as previously described. The third individual probe would contain a coil of fine wire, as previously described for third section 130 of probe 102. The wire would in turn be connected to a voltmeter. Therefore, in operation, the first separate probe would be inserted into the heat exchanger tube and be used to demagnetize the magnetite as previously described. It would then be removed and the second individual probe would be inserted into the heat exchanger tube and be used to magnetize the magnetite by a known amount. After this process, the second individual probe would be removed and the third individual probe would be inserted into the heat exchanger tube and the probe moved up and down within the tube and the voltge measured at various locations, as previously described. In essence, the three individual probe method is far more cumbersome than the single probe method, but it can be used, especialy where only very tiny probes can be fit into the heat exchanger tubes.

In addition to the apparatus, the present invention also includes the method as described above. The method involves obtaining a sample of the tubing used in the heat exchanger to be measured and coating the tubing with various quantities of magnetite along its length. At each given length along the sample tube whose diameter and wall thickness are known, the thickness of magnetite is known. The magnetite is then magnetized by running a coil of direct current through the sample tube. After this operation, a coil of finely wound wire is run through the tube and the voltage at each location is measured. With the voltage, the velocity of movement of the coil and the thickness of magnetite known, the calibration constants for the specific tubing are calculated by the formula:

$$k_1 k_2 = \frac{V}{vMG}$$

where V is the measured voltage, v is the velocity of movement of the coil, and MG is the thickness of the magnetite at the location where the voltage is measured.

With the above known, the thickness of magnetite at given locations along the heat exchanger can be measured by the following means. Demagnetizing means (as previously described) are used to demagnetize the magnetite along the length of the coil to start at a known zero magnetization. After this, magnetizing means are used to magnetize the magnetite (as previously described) along the length of the heat exchanger tubes. The third step in the process involves running a coil of fine wire (as previously described) up or down the heat exchanger tube and measuring the voltage induced in the coil at given locations along the length of the heat exchanger tube. Knowing the voltage at a location and velocity of movement of the coil through the tube, the thickness of magnetite at the location can be measured by the formula:

$$MG = \frac{V}{k_1 k_2 v}$$

Of course the present invention is not intended to be restricted to any particular form or arrangement, or any specific embodiment disclosed herein, or any specific use, since the same may be modified in various particulars or relations without departing from the spirit or scope of the claimed invention herein above shown and described of which the method and apparatus shown is intended only for illustration and for disclosure of an operative embodiment and not to show all of the various forms of modification in which the invention might be embodied.

The invention has been described in considerable detail in order to comply with the patent laws by providing a full public disclosure of at least one of its forms. However, such detailed description is not intended in any way to limit the broad features or principles of the invention, or the scope of patent monopoly to be granted.

What is claimed is:

1. A method of measuring the amount of magnetite which has adhered to a heat exchanger tube located within a heat exchanger, comprising:
   a. obtaining a sample of the type of heat exchanger tube that is used in the heat exchanger that will be tested, coating said sample tube with varying thicknesses of magnetite along the length of said sample tube, magnetizing the magnetite on said sample tube, running a measuring coil through said sample tube at known speed, and measuring the voltage induced in said measuring coil at various locations along the length of said sample tube where the magnetite thickness is known, to arrive at calibration constants for the heat exchanger tube to be tested;
   b. magnetizing the magnetite on the heat exchanger tube by magnetizing means;
   c. running a coil connected to a voltmeter through said heat exchanger tube at a known velocity and measuring the voltage induced into the coil at given locations along the heat exchanger tube; and
   d. calculating the thickness of adhered magnetite at various locations along the length of the heat exchanger tube by multiplying the calibration constants for the tube by the velocity with which the coil was moved through the heat exchanger tube and dividing this multiple into a voltage induced at a location to obtain the magnetite thickness at the location.

2. The method in accordance with claim 1 further comprising the step of demagnetizing the magnetite on the heat exchanger tubes by use of demagnetizing means, said demagnetizing step performed prior to said magnetizing step.

3. The method in accordance with claim 2 wherein the demagnetizing means is a coil of wire which is energized by a source of alternating current, said coil being wound on a probe which may be positioned within the heat exchanger tube.

4. The method in accordance with claim 1 further comprising the step of demagnetizing the magnetite on the heat exchanger tube by use of demagnetizing means, said demagnetizing step performed after the step of running a coil connected to a voltmeter through said heat exchanger tube.

5. The method in accordance with claim 4 wherein the demagnetizing means is a coil of wire which is energized by a source of alternating current, said coil being wound on a probe which may be positioned within the heat exchanger tube.

6. The method in accordance with claim 1 wherein the tube is a nickel alloy steel, such as Inconel.

7. The method in accordance with claim 1 wherein the magnetizing means is a coil of wire which is energized by a source of direct current, said coil being wound on a probe which may be positioned within the heat exchanger tube.

8. The method in accordance with claim 1 wherein the voltage measuring coil is wound on a probe which may be moved within the heat exchanger tube.

* * * * *